United States Patent
Raz

(10) Patent No.: US 9,326,693 B2
(45) Date of Patent: May 3, 2016

(54) PLACEMENT OF ELECTRODES IN PROXIMITY TO THE HEART

(71) Applicant: BIOSENSE WEBSTER (ISRAEL) LTD., Yokneam (IL)

(72) Inventor: Shaul Haim Raz, Shimshit (IL)

(73) Assignee: Biosense Webster (Israel) Ltd. (IE)

( * ) Notice: Subject to any disclaimer, the term of this patent is extended or adjusted under 35 U.S.C. 154(b) by 45 days.

(21) Appl. No.: 14/253,209

(22) Filed: Apr. 15, 2014

(65) Prior Publication Data

US 2015/0289776 A1   Oct. 15, 2015

(51) Int. Cl.
| A61N 1/00 | (2006.01) |
| A61B 5/04 | (2006.01) |
| A61B 5/0408 | (2006.01) |
| A61B 5/06 | (2006.01) |

(52) U.S. Cl.
CPC ........... *A61B 5/04012* (2013.01); *A61B 5/0408* (2013.01); *A61B 5/04085* (2013.01); *A61B 5/063* (2013.01)

(58) Field of Classification Search
CPC .................................................... A61B 5/0452
USPC ........................................ 600/509, 518, 523
See application file for complete search history.

(56) References Cited

U.S. PATENT DOCUMENTS

| 4,692,148 A | 9/1987 | Kantrowitz et al. |
| 4,909,261 A | 3/1990 | Rothenberg |
| 7,536,218 B2 | 5/2009 | Govari et al. |
| 8,456,182 B2 | 6/2013 | Bar-Tal et al. |
| 2010/0079158 A1* | 4/2010 | Bar-Tal et al. ................ 324/705 |
| 2012/0059270 A1 | 3/2012 | Grunwald |
| 2012/0101357 A1 | 4/2012 | Hoskuldsson et al. |
| 2012/0172738 A1 | 7/2012 | Gleich |
| 2013/0204149 A1 | 8/2013 | Hwang et al. |

OTHER PUBLICATIONS

Miller, III, Walter T. et al., "Total body surface potential mapping during exercise: QRS-T-wave changes in normal young adults", Circulation 62, pp. 632-645, No. 3.

Harrigan, Richard A. et al., "Electrocardiographic Electrode Misplacement, Misconnection, and Artifact", The Journal of Emergency Medicine, vol. 43, No. 6, Dec. 2012, pp. 1038-1044.

Xia, Henian et al., "Paper; Automatic detection of ECG electrode misplacement: a tale of two algorithms, Automatic detection of ECG electrode misplacement: a tale of two algorithms", Physiological Measurement, Institute of Physics Publishing, Bristol, GB, vol. 33, No. 9, Aug. 2012, pp. 1549-1561.

* cited by examiner

*Primary Examiner* — Nicole F Lavert
*Assistant Examiner* — Nadia A Mahmood

(57) ABSTRACT

A method, consisting of receiving respective electrocardiograph (ECG) signals from body-surface electrodes at respective locations in proximity to a heart of a subject. The ECG signals may be processed to generate respective signal parameters characteristic of positions of the body-surface electrodes with respect to the heart, and the respective locations may be adjusted so as to achieve a specified geometrical relationship between the body-surface electrodes and the heart in response to the respective signal parameters.

28 Claims, 4 Drawing Sheets

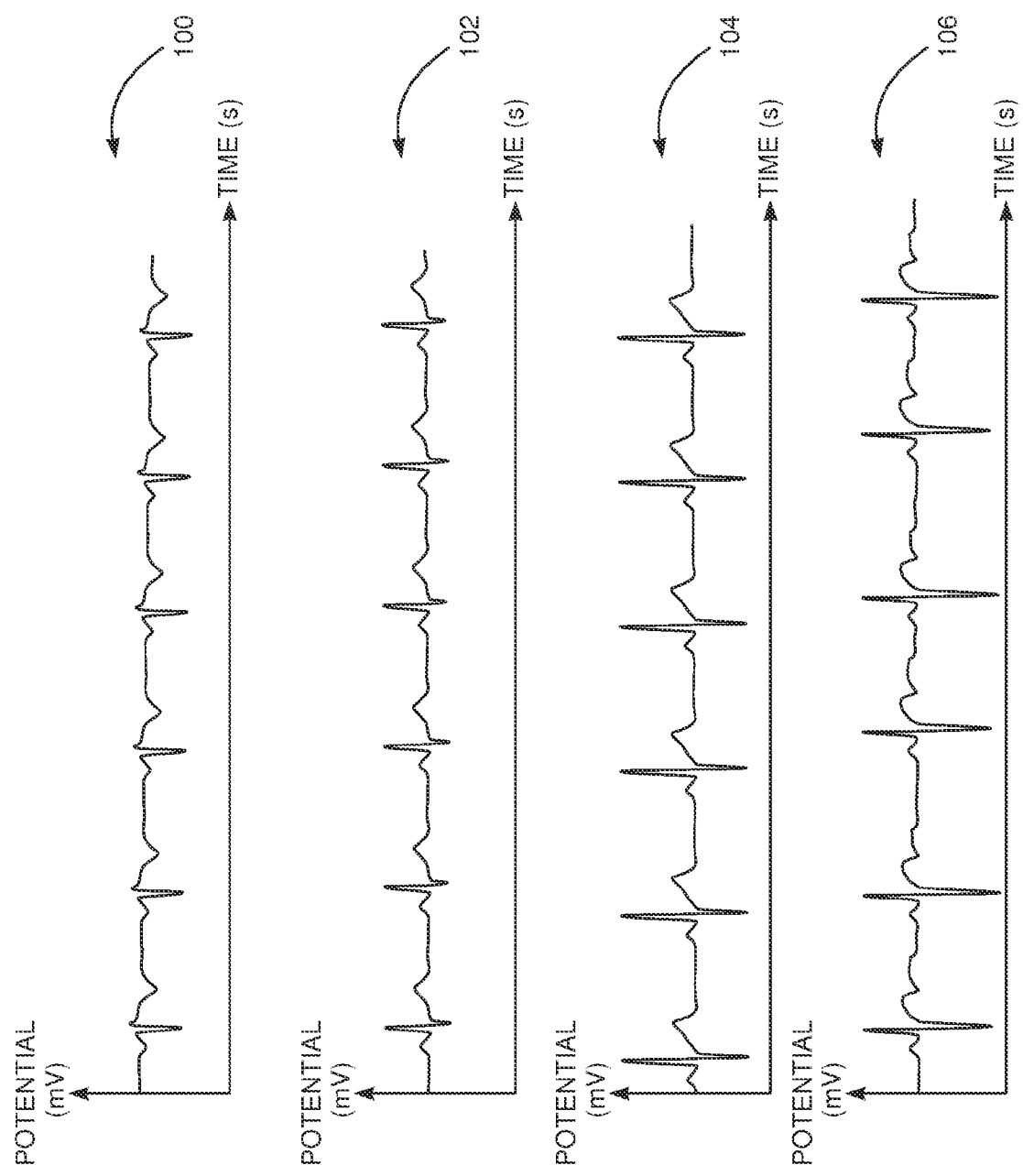

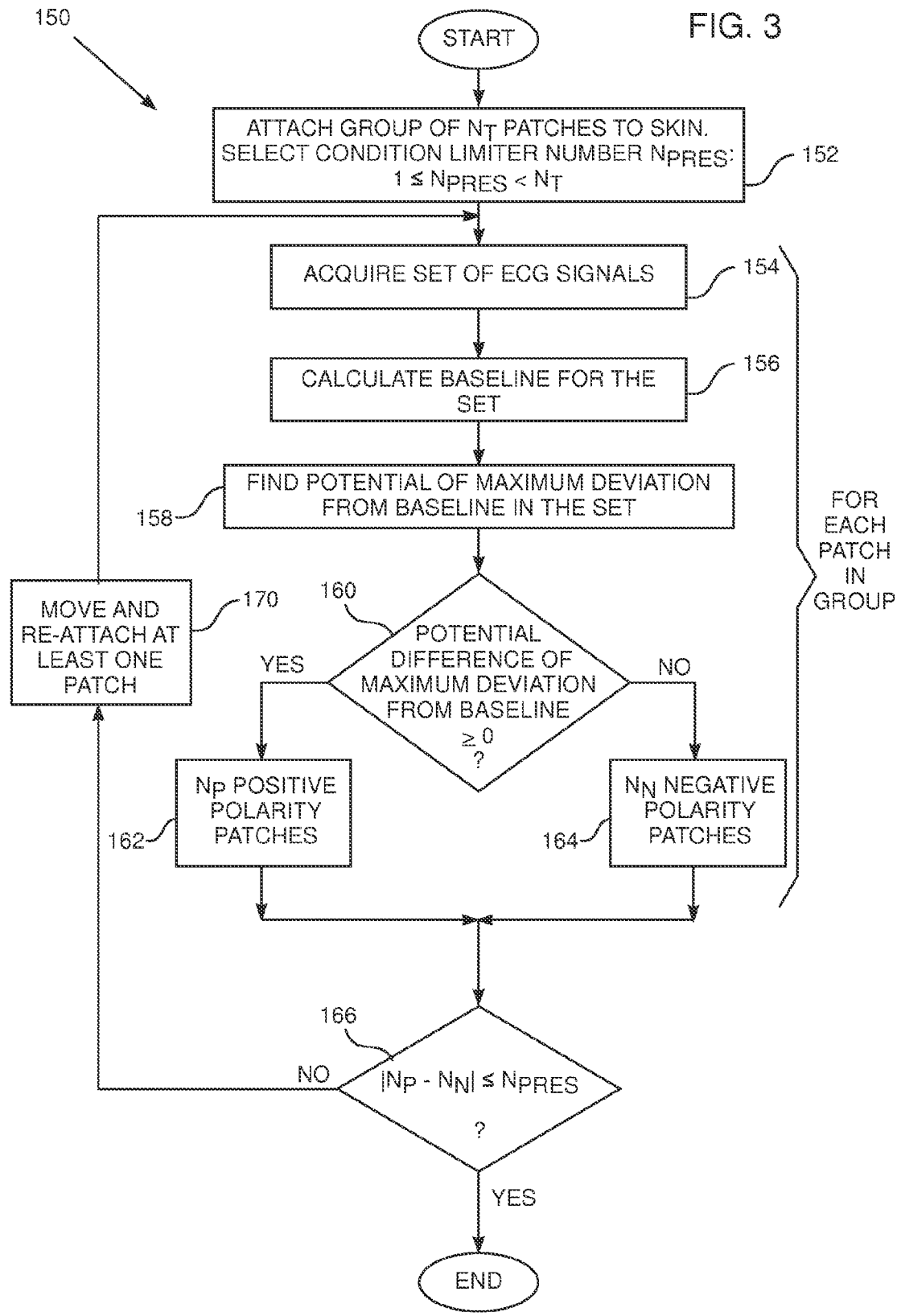

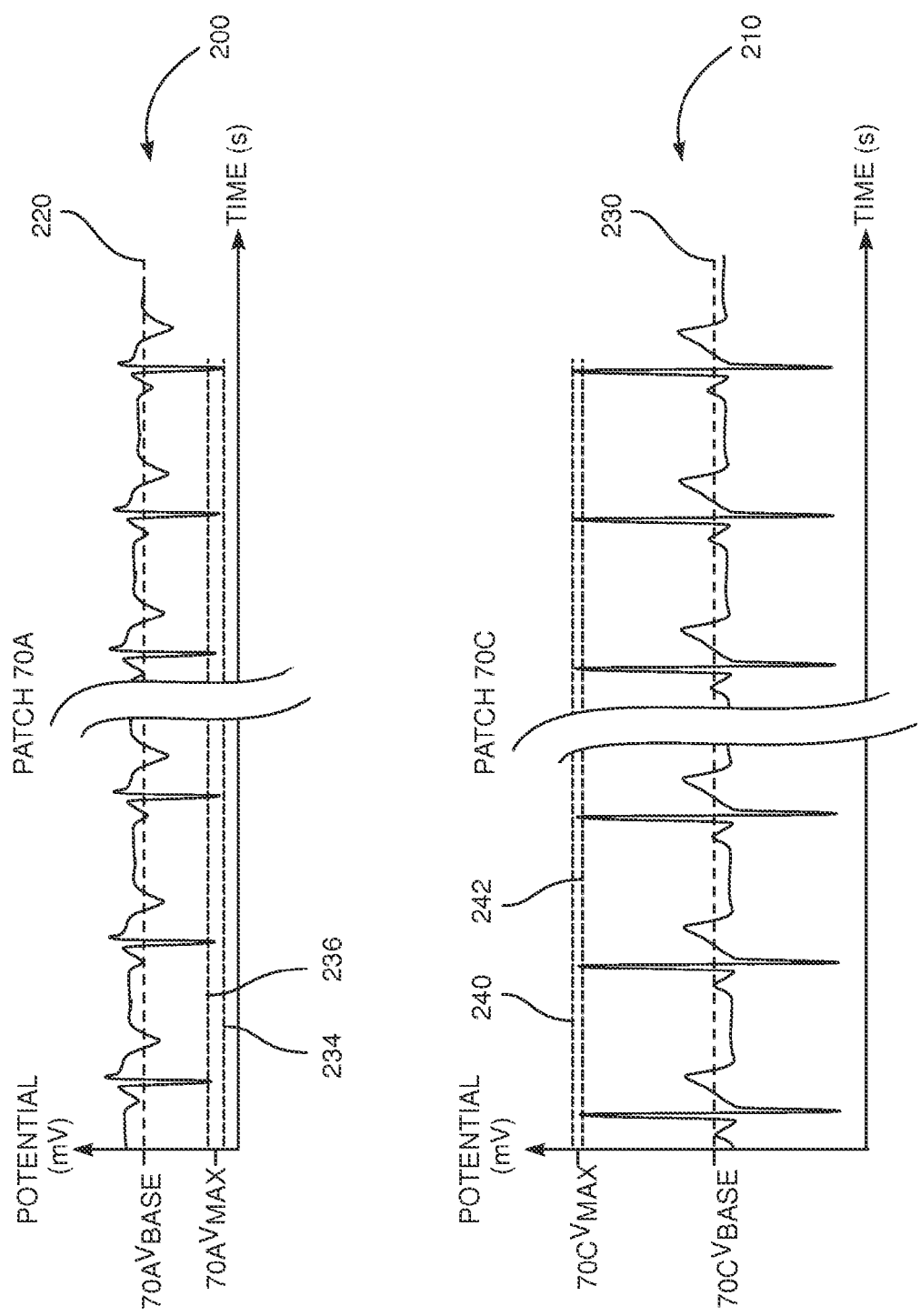

PLACEMENT OF ELECTRODES IN PROXIMITY TO THE HEART

FIELD OF THE INVENTION

The present invention relates generally to positioning of electrodes, and specifically to positioning electrodes on the skin of a subject undergoing a medical procedure.

BACKGROUND OF THE INVENTION

U.S. Pat. No. 8,456,182 to Bar-Tal et al, whose disclosure is incorporated herein by reference, describes positioning body-electrodes in galvanic contact with a body of a patient and positioning a mapping-tool, having a mapping-electrode, in a plurality of regions in the body. The disclosure describes generating a set of calibration-currents between the body-electrodes and the mapping-electrode at different positions of the mapping-tool in the region.

U.S. Pat. No. 7,536,218 to Govari et al, whose disclosure is incorporated herein by reference, describes a position sensing system that includes a probe adapted to be introduced into a body cavity of a subject. The probe includes at least one probe electrode. A control unit measures an impedance between the at least one probe electrodes and one or more points on a body surface of the subject.

U.S. Patent Application 2012/0101357 to Hoskuldsson et al, whose disclosure is incorporated herein by reference, describes a thorax belt that is placed around a body at a point above the heart-position, while an abdomen belt is placed at a point below the heart-position. The disclosure claims that the electronic field caused by the heart appears between the belts.

U.S. Patent Application 2013/0204149 to Hwang et al, whose disclosure is incorporated herein by reference, describes an apparatus and a method to generate an atrial fibrillation prediction model. The model extracts features in a predetermined time period from electrocardiogram data.

U.S. Patent Application 2012/0059270 to Grunwald, whose disclosure is incorporated herein by reference, describes devices and methods for obtaining and using endovascular electrograms in a number of clinical applications and settings. U.S. Patent Application 2012/0172738 to Gleich, whose disclosure is incorporated herein by reference, describes an apparatus and a corresponding method for non-invasive intracardiac electrocardiography (ECG) by use of a magnetic and electrically conducting interference device.

An article entitled "Total Body Surface Potential Mapping During Exercise: QRS-T-wave Changes in Normal Young Adults," by Miller III et al., published in Circulation 62, No. 3, 1980, is incorporated herein by reference. The article provides maps of body surface potential distributions.

The description above is presented as a general overview of related art in this field and should not be construed as an admission that any of the information it contains constitutes prior art against the present patent application.

SUMMARY OF THE INVENTION

An embodiment of the present invention provides a method, including: receiving respective electrocardiograph (ECG) signals from body-surface electrodes at respective locations in proximity to a heart of a subject;

processing the ECG signals to generate respective signal parameters thereof characteristic of positions of the body-surface electrodes with respect to the heart; and adjusting the respective locations so as to achieve a specified geometrical relationship between the body-surface electrodes and the heart in response to the respective signal parameters.

Typically the body-surface electrodes are configured to receive currents, from a catheter electrode within the subject, indicative of a location of the catheter electrode. Receiving the respective ECG signals may include receiving the ECG signals while not receiving the currents. Alternatively, receiving the respective ECG signals may include receiving the ECG signals while receiving the currents.

In a disclosed embodiment the geometric relationship consists of the body-surface electrodes surrounding the heart.

In an alternative embodiment processing the ECG signals includes finding baselines for the signals, and generating the signal parameters includes determining whether differences between maximum deviations from the baselines are positive or negative. The method may include enumerating as a first number the body-surface electrodes having a positive difference, and enumerating as a second number the body-surface electrodes having a negative difference, so that achieving the specified geometrical relationship consists of the first and the second numbers differing by no more than a preset number. The preset number may be a positive whole number less than a total number of the body-surface electrodes.

In an further alternative embodiment the method includes dividing the body-surface electrodes into a plurality of sub-groups, and, for a given sub-group enumerating as a first number the body-surface electrodes therein having a positive difference, and enumerating as a second number the body-surface electrodes therein having a negative difference, so that achieving the specified geometrical relationship consists of the first and the second numbers differing by no more than a preset number for the given sub-group. The preset number may be a positive whole number less than a total number of the body-surface electrodes in the given sub-group.

The signal parameters may include binary parameters. Alternatively or additionally, the signal parameters may include non-binary parameters.

There is further provided, according to an embodiment of the present invention, apparatus, including:

body-surface electrodes configured to receive respective electrocardiograph (ECG) signals from respective locations in proximity to a heart of a subject; and a controller, configured to:

process the ECG signals to generate respective signal parameters thereof characteristic of positions of the body-surface electrodes with respect to the heart, and adjust the respective locations so as to achieve a specified geometrical relationship between the body-surface electrodes and the heart in response to the respective signal parameters.

The present invention will be more fully understood from the following detailed description of the embodiments thereof, taken together with the drawings in which:

BRIEF DESCRIPTION OF THE DRAWINGS

FIG. 2 schematically illustrates graphs of electrocardiograph (ECG) signals acquired by patches in different locations on a subject, according to an embodiment of the present invention;

FIG. 3 is a flowchart of steps describing processing for the system of FIG. 1, according to an embodiment of the present invention; and FIG. 4 shows graphs illustrating some of the steps of the flowchart, according to an embodiment of the present invention.

DETAILED DESCRIPTION OF EMBODIMENTS

Overview

Figure 1:
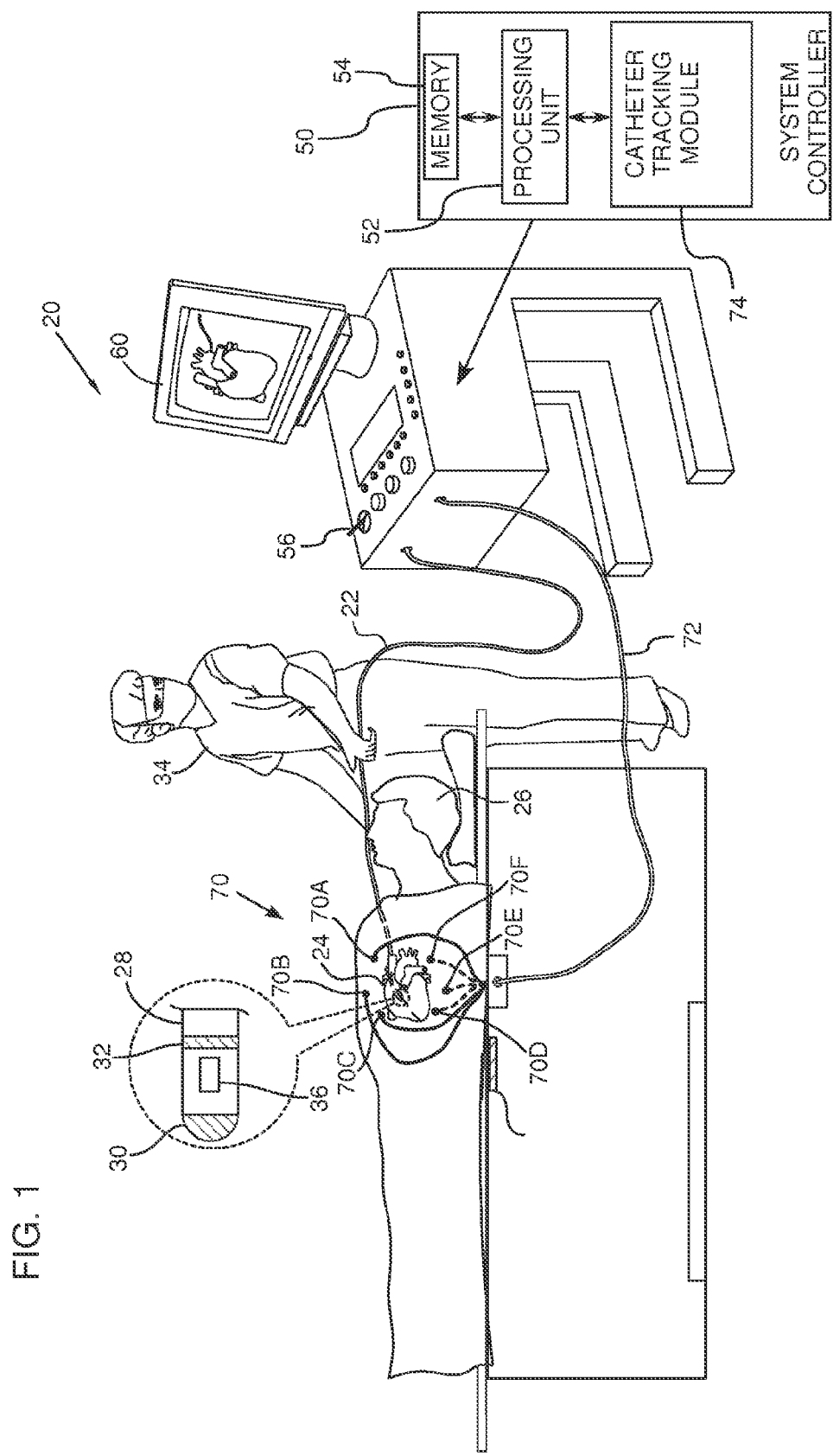
FIG. 1 is a schematic, pictorial illustration of an electrode positioning system, according to embodiments of the present invention.

An embodiment of the present invention provides a system that may be used to optimize tracking of a probe within or in proximity to the heart of a subject, where the tracking is performed by measuring and analyzing impedances between the probe and electrodes attached to the skin of the subject. The impedances are typically calculated by injecting a current into the probe, measuring the current transferring through respective electrodes, and estimating the different impedances between the probe and the respective electrodes from the measured currents.

The skin electrodes are attached at locations on the subject's skin that are in the region of the heart. Because of their proximity to the heart, the electrodes receive electrocardiograph (ECG) signals from the beating heart, and embodiments of the present invention process the ECG signals to derive respective parameters of the signals that are characteristic of the positions of the skin electrodes relative to the heart.

Using the derived signal parameters an operator of the system may adjust locations of the skin electrodes so as to achieve a specified geometrical relationship between the electrodes and the heart.

In one embodiment the signal parameter derived for a given signal is a "polarity" of the signal, where the polarity corresponds to the sign of the difference between the largest peak of the signal and the signal baseline. Thus the polarity of the signal is a binary quantity that can be positive or negative.

The geometrical relationship may correspond to the electrodes surrounding the heart. Using the example of the polarities described above, in a disclosed embodiment the electrodes may be assumed to surround the heart, so achieving the geometrical relationship, if (for an even number of electrodes) there are equal numbers of positive and negative polarities for the electrode signals. If there is an odd number of electrodes, they may be assumed to surround the heart if the numbers of positive and negative polarities differ by one.

In an alternative embodiment, the electrodes may be assumed to achieve a specified geometrical relationship, such as surrounding the heart, if the difference between the numbers of positive and negative polarity electrodes is less than a preset number that is greater than one but less than the total number of electrodes.

For example, if there are 7 electrodes, then in the disclosed embodiment described above the electrodes achieve the geometrical relationship if there are 4 electrodes of one polarity and 3 electrodes of the other polarity, so that the numbers of electrodes differ by one. For the alternative embodiment the preset number (for 7 electrodes) may be set to be any whole number from 2 to 6. If it is set equal to 6 (so that the numbers of electrodes can differ by up to 5), then the geometrical relationship is satisfied for 4 and 3 electrodes of opposite polarities, or 5 and 2 opposite polarity electrodes, or 6 and 1 opposite polarity electrodes.

DETAILED DESCRIPTION

Reference is now made to FIG. 1, which is a schematic, pictorial illustration of an electrode positioning system 20, according to embodiments of the present invention. In system 20, a catheter 22 is inserted into a lumen, such as a chamber of a heart 24 of a subject 26 wherein a medical procedure, such as ablation of the heart tissue, is to be performed. At a distal end 28 of the catheter there are one or more electrodes, and by way of example two electrodes 30, 32 are shown in the figure. As is explained below, at least one of the electrodes at the distal end, herein assumed to be electrode 30 at the tip of the distal end, is used by system 20. The catheter is manipulated by a medical practitioner 34 during the procedure, so as to position electrodes 30, 32 in desired locations, and each electrode at the distal end, including electrode 30, may perform multiple functions. For example, the electrodes may be configured to perform ablation of tissue of the heart and/or to measure potentials of heart tissue. Depending on the procedure being performed, the distal end may comprise other elements; by way of example distal end 28 comprises a force sensor 36.

The functioning of system 20 is managed by a system controller (SC) 50, comprising a processing unit 52 communicating with a memory 54, wherein is stored software for operation of system 20. Controller 50 is typically an industry-standard personal computer (PC) comprising a general-purpose computer processor. However, in some embodiments, at least some of the functions of the controller are performed using custom-designed hardware and software, such as an application specific integrated circuit (ASIC) or a field programmable gate array (FPGA). Controller 50 is typically operated by practitioner 34 using a pointing device 56 and a display 60, which enable the practitioner to set parameters of system 20. Display 60 typically also presents results of the procedure to the medical practitioner.

The software in memory 54 may be downloaded to the controller in electronic form, over a network, for example. Alternatively or additionally, the software may be provided on non-transitory tangible media, such as optical, magnetic, or electronic storage media.

A plurality of substantially similar body-surface electrodes 70, such as adhesive skin patches, and also referred to herein as patches 70, are coupled to the body-surface (i.e., the skin) of subject 26 in general proximity to heart 24. As necessary, in the description herein patches 70 are distinguished from each other by appending a letter to the identifying numeral 70 of the patches. By way of example, except where otherwise stated, in the following description there are assumed to be three patches 70A, 70B, and 70C applied to the chest of subject 26, and three patches 70D, 70E, and 70F applied to the back of the subject. A generic patch may be referred to as patch 70N.

In some embodiments practitioner 34 may be able to identify individual patches 70, for example by the patches and/or their leads being color coded or marked with an identifying letter or number. A use by system 20 for such identification is described below.

During the medical procedure referred to above, system controller 50 injects an alternating current into electrode 30, via cabling in catheter 22. The injected current returns to the system controller via patches 70, and via cabling 72 connecting the patches to the system controller. Using a catheter tracking module 74 the system controller analyzes the different alternating returning currents, and determines position coordinates of the distal tip in, or in proximity to, heart 24 based on the returning currents from each of patches 70. Using the determined position coordinates, the system controller is able to show the location of the distal tip inside the heart on display 60. Such a location system, measuring the location of the distal tip by measuring currents from the tip received by patches 70, is herein termed a current location system. U.S. Pat. No. 8,456,182 to Bar-Tal et al. which is referenced above, describes such a system.

In order to optimize the measurements of the position coordinates of the distal tip, patches 70 should surround the heart. As is described herein, system 20 determines positions for the patches so that the patches satisfy this geometrical relationship.

The distal tip may also be tracked by other systems known in the art, for example, by a magnetic tracking system. One such magnetic tracking system is the CARTO 3 system, produced by Biosense Webster, Inc, Diamond Bar, Calif., which tracks the distal tip by using alternating magnetic fields to induce corresponding positioning currents in coils in the tip. The fields are typically set to alternate at frequencies of 1-3 kHz, but may be set to alternate at higher frequencies, up to 50 kHz or more.

In addition to patches 70 being used to acquire the returning currents, each of the patches also receives electrocardiograph (ECG) signals generated by heart 24, and the ECG signals are transferred by cabling 72 to system controller 50. It will be understood that the ECG signals are received by patches 70 regardless of the presence of the different alternating returning currents, i.e., the ECG signals are received by the patches even if no alternating current is injected into electrode 30.

The received ECG signals acquired by patches 70 are dependent on the locations of the patches with respect to heart 24, and vary significantly from location to location. Examples of typical ECG signals are illustrated in FIG. 2 below.

FIG. 2 schematically illustrates graphs of ECG signals acquired by patches 70 in different locations on subject 26, according to an embodiment of the present invention. All graphs are assumed to be generated by heart 24 as it beats, so that although there are variations in the graphs, such as the shape of the acquired signals as well as phase differences between the signals, there are also consistent parameters, such as the period of the signals. The ECG signals are assumed to be unipolar signals, with the potential of the signals being measured with reference to an arbitrary reference, typically the Wilson central terminal (WCT) reference. By way of example a graph 100 is assumed to correspond to the ECG signal acquired by patch 70A, a graph 102 is assumed to correspond to the ECG signal acquired by patch 70C, a graph 104 is assumed to correspond to the ECG signal acquired by patch 70D, and a graph 106 is assumed to correspond to the ECG signal acquired by patch 70F.

Embodiments of the present invention process the ECG signals from each of patches 70 to generate respective signal parameters that are characteristic of the position of the patch acquiring the signal.

FIG. 3 is a flowchart 150 of steps describing the processing of the ECG signals, and how the signal parameters are used to check if the arrangement of patches 70 satisfies a geometrical relationship between the patches and the heart, and FIG. 4 shows graphs illustrating some of the steps of the flowchart, according to an embodiment of the present invention. All the steps of the flowchart may typically be applied prior to the medical procedure referred to above being initiated, but in some embodiments the steps of the flowchart may be applied while the procedure is being performed.

For clarity and simplicity, in the following description the geometrical relationship checked in the flowchart is assumed to be that patches 70 surround the heart. However, a person having ordinary skill in the art will be able to adapt the description, mutatis mutandis, for other geometrical relationships, such as that the patches do not surround the heart, or that the patches are on one side of the heart, and all such geometrical relationships are included in the scope of the present invention.

In a first step 152, practitioner 34 attaches a group of $N_T$ patches 70 to the skin of the patient, where $N_T$ is the number of patches attached. In the following description, except as stated below, the group attached is assumed to comprise six patches 70A, ... 70F, so that $N_T=6$. Patches 70 are typically attached so that there is a predetermined separation between "nearest-neighbor" patches, the predetermined separation typically being in the range of 20 cm-25 cm, although the separation may be larger or smaller than values in this range.

Also in first step 152, practitioner 34 selects a preset number, $N_{PRES}$, to be used by controller 50 in evaluating a condition 166 applied to the group of patches. $N_{PRES}$ may be considered to be a measure of an allowable variation between different types of patches in the group of patches, and acts as a condition limiter on the allowable variation, as is explained in more detail below. $N_{PRES}$, also referred to herein as the condition limiter number, is selected so that the following condition is valid:

$$1 \le N_{PRES} < N_T \quad (1)$$

where $N_T$ is as defined above, i.e., is the total number of patches in the group.

For simplicity, while the following description for steps 154-164 is written for the actions performed by controller 50 in analyzing the ECG signals acquired by patches 70A and 70C, it will be understood that the controller performs the actions for each patch in the group of patches 70.

In an acquisition step 154, the controller acquires and stores respective sets of ECG signals from patch 70A and from patch 70C. Each set of ECG signals comprises a set of ordered pairs of the potential registered at the patch at a given time. In one embodiment the acquisition is over a preset period of time, for example 10 s, so that approximately ten periods of the ECG signals are acquired. Typical graphs of the acquired signals are graphs 200 and 210, which are enlargements of respective graphs 100 and 104 (FIG. 2).

In a baseline calculation step 156, the controller calculates an arithmetic average of the respective stored potentials of each set, and assumes that the average corresponds to the baseline of the respective signal. A broken line 220 illustrates the baseline potential $_{70A}V_{BASE}$ calculated for patch 70A, and a broken line 230 illustrates the baseline potential $_{70C}V_{BASE}$ calculated for patch 70C.

In an analysis step 158, the controller analyzes the stored signals to find the value of the maximum deviation of the stored potentials of each period of the signal from the baseline potential. Typically, although not necessarily, the value of each maximum deviation occurs during the QRS complex of the ECG signals. Normally, and as assumed herein, the values of the maximum deviations lie within a relatively narrow range of values, which are different from each other because of inherent variations of the generated signals, as well as because of inherent noise in the signals.

Thus, the maximum deviations for patch 70A are assumed to lie within values corresponding to broken lines 234, 236, and the maximum deviations for patch 70C are assumed to lie within values corresponding to broken lines 240, 242. To allow for the differences referred to above in the maximum deviations, the controller averages the maximum deviations for each patch, to find mean maximum deviations. Graph 200 illustrates a mean maximum deviation $_{70A}V_{MAX}$ for patch 70A, and graph 210 illustrates a mean maximum deviation $_{70C}V_{MAX}$ for patch 70C.

In a comparison step 160, the controller calculates a difference between the mean maximum deviation for each patch and the patches baseline value according to equation (2):

$$D_{70N} = {_{70N}V_{MAX}} - {_{70N}V_{BASE}} \quad (2)$$

where $D_{70N}$ is a difference for patch 70N, ${_{70N}V_{MAX}}$ is the maximum potential deviation for patch 70N, and ${_{70N}V_{BASE}}$ is the baseline potential for patch 70N.

In step 160 the controller determines if $D_{70N}$ is positive, i.e., if $D_{70N} \geq 0$, or if the difference is negative, i.e., if $D_{70N} < 0$.

If the difference is positive, then in a first polarity step 162 the controller assigns the polarity of the patch to be positive, and determines a number of positive polarity patches $N_P$. If the difference is negative, then in a second polarity step 164 the controller assigns the polarity of the patch to be negative, and determines a number of negative polarity patches $N_N$.

As stated above, the controller performs steps 154-164 for each of patches 70, and so determines a polarity for each of the patches.

The inventors have found that, for a given patch 70, the polarity provides a good determinant of the position of the patch with respect to heart 24. A possible explanation of this property of the polarity is, that to a first approximation, heart 24 may be considered to be a radiating dipole, with a dipole axis on a line between the right shoulder and the left leg. Such a dipole defines a surface that is orthogonal to the line, and that passes through a point on the line representing the position of the heart.

On one side of the surface, the dipole radiation from the heart has a first phase, and on the other side of the surface the dipole radiation has a second phase that is 180° to the first phase. The polarity evaluated by controller 50 is a measure of the phase of the dipole signal radiated by the heart. Patches having the same polarity may thus be assumed to be on one side of the surface defined above; patches having opposite polarities may be assumed to be on opposite sides of the surface.

In a comparison step 166 the controller evaluates an absolute value of the difference between the number of positive polarity patches $N_P$ and the number of negative polarity patches $N_N$. The absolute value provides an indication to the controller of the relative numbers of patches 70 on the two sides of the surface defined above, and in comparison step 166 the controller checks if the absolute value is less than or equal to the condition limiter number set in step 152. I.e., the controller checks if the following inequality is valid:

$$|N_P - N_N| \leq N_{PRES} \quad (3)$$

If the controller determines that the preset condition for comparison step 166 is valid, then a message may be shown on display 60 informing the practitioner that the patches are in valid locations, i.e., that they surround the heart and that the desired geometrical relationship has been achieved, and the flowchart ends. If the controller determines that the preset condition for comparison step 166 is invalid, then the flowchart continues to a move patch step 170, wherein at least one of the patches is moved and re-attached. From step 170 the flowchart returns to step 154 and the controller reiterates steps 154-166 for all patches in the group, until step 166 is valid.

Typically in step 170 a message may be shown on display 60 informing the practitioner that the patches do not surround the heart and that at least one patch should be moved.

As stated above, in some embodiments practitioner 34 is able to identify individual patches 70. In these cases controller 50 may incorporate into the message a suggestion for which patch or patches could be moved, so that the preset condition of step 166 becomes valid.

Referring back to the description for step 152, as stated there, $N_{PRES}$ acts as a condition limiter on an allowable variation between numbers of positive and negative patches. A small value for $N_{PRES}$ means that there is little allowable variation between the numbers of patches, a large value for $N_{PRES}$ means that the variation between the patch numbers is greater.

For example, for a group of six patches 70 $N_T=6$, so that $N_{PRES}$ may be, from equation (1), any whole number from 1 to 5. If in step 152 $N_{PRES}$ is set equal to 1, then the only values satisfying equation (3), i.e., for comparison step 166, and thus the geometrical relationship, to be valid, are $N_P=N_N=3$. However, if in step 152 $N_{PRES}$ is set equal to 5, then possible values satisfying equation (3), so that the geometrical relationship is considered valid, are $N_P=5$, $N_N=1$; $N_P=4$, $N_N=2$; $N_P=N_N=3$; $N_P=2$, $N_N=4$; and $N_P=1$, $N_N=5$.

Flowchart 150 may be used to evaluate if all attached patches, taken together as one group, satisfy a geometrical relationship. Alternatively or additionally, the flowchart may be used to evaluate if different sub-groups of attached patches satisfy respective geometrical relationships.

For example, there may be 8 patches 70 in total attached to subject 26. Considering all the patches as one group, $N_T=8$, so that $N_{PRES}$ may be, from equation (1), any whole number from 1 to 7. For example, if $N_{PRES}$ is set equal to 3, then possible values satisfying equation (3), so that the geometrical relationship is considered valid, are $N_P=5$, $N_N=3$; $N_P=N_N=4$; and $N_P=3$, $N_N=5$.

The group of 8 patches 70 may, by way of example, be divided into a first sub-group of 5 patches 70 applied to the chest of subject 26, and a second sub-group of three patches 70 applied to the back of the subject. In the following description, variables such as the numbers of patches in each sub-group are distinguished by prefacing the variable with an identifying sub-script. Thus, for the two sub-groups assumed herein, $_1N_T=5$ and $_2N_T=3$, where the "1" sub-script corresponds to the chest sub-group, and the "2" sub-script corresponds to the back sub-group.

The first sub-group has $_1N_T=5$, so that $_1N_{PRES}$ may be any whole number from 1 to 4. If, for example, $_1N_{PRES}$ is set equal to 3, then possible values satisfying equation (3), so that a geometrical relationship for the chest sub-group is considered valid, are $_1N_P=4$, $_1N_N=1$; $_1N_P=3$, $_1N_N=2$; $_1N_P=2$, $_1N_P=3$; and $_1N_P=1$, $_1N_N=4$.

The second sub-group has $_2N_T=3$, so that $_2N_{PRES}$ may be 1 or 2. In this case, for either $_2N_{PRES}$ set to equal 1 or 2, the only possible values satisfying equation (3), so that a geometrical relationship for the back sub-group is considered valid, are $_2N_P=2$, $_2N_N=1$; and $_2N_P=1$, $_2N_N=2$.

If sub-groups of patches 70, such as those exemplified above for 8 patches, are defined, then practitioner 34 may use any combination of the geometrical relationships, i.e., the comparisons of step 166, to check if an overall geometrical relationship for the patches has been achieved. Thus, in the example above, the practitioner may require that the comparisons of all three geometrical relationships, i.e. for the whole group and both sub-groups, be valid. Alternatively, the practitioner may require that the comparisons of any two geometrical relationships, e.g. for both sub-groups be valid. Further alternatively, the practitioner may require that the comparison of any one of the geometrical relationships, e.g. the chest sub-group or the whole group, be valid.

As another example, applying flowchart 150 to the six patches 70A, 70B, . . . , 70F taken as a whole group and assuming $N_{PRES}$ is set equal to 1, then comparison step 166 is valid if any three of the patches have positive polarities, and if the remaining three patches have negative polarities.

The six patches 70A, 70B, ..., 70F may be divided into two sub-groups, a chest sub-group of patches 70A, 70B, and 70C, and a back sub-group of patches 70D, 70E, and 70F, and flowchart 150 may be applied to each sub-group. If for each sub-group $_SN_{PRES}$ is set equal to 1 (where S is a sub-group identifier, herein equal to 1 or 2), then for the chest sub-group comparison step 166 is valid if $_1N_P=2$, $_1N_N=1$; or $_1N_P=1$, $_1N_N=2$. For the back sub-group comparison step 166 is valid if $_2N_P=2$, $_2N_N=1$; or $_2N_P=1$, $_2N_N=2$.

For the examples above the practitioner may require, as a relatively strict constraint in order to achieve the geometrical relationship, that the comparisons described above for the whole group and both sub-groups be valid. For a less strict constraint the practitioner may require that only the comparisons for the two sub-groups be valid.

Other possible combinations and subcombinations of comparisons, for groups and sub-groups of patches, in order that an overall geometrical relationship be achieved, will be apparent to those having ordinary skill in the art, and all such combinations and subcombinations are assumed to be comprised within the scope of the present invention.

The analysis described above derives a signal parameter for each patch 70, the polarity, by processing the ECG signals from the respective patches. The controller uses the signal parameters to check that the patches are in a required geometrical relationship with respect to the heart, e.g., that they surround the heart. The polarity is a binary parameter, and those having ordinary skill in the art will be aware of other binary signal parameters that the controller may use to check that the geometrical relationship has been achieved. Such binary parameters include, but are not limited to, the amplitude of the ECG signal being greater than or less than a predetermined amplitude value, and the phase of the ECG signal being greater than or less than a predetermined phase value.

In addition it will be understood that the signal parameter derived from the ECG signals is not necessarily binary, and may be a non-binary parameter, such as a rational number. The binary polarity parameter described above assigns a binary value to the ECG signal, and its respective patch, according to whether the maximum deviation from the baseline is above or below the baseline. The binary value of the maximum deviation could be incorporated into the polarity, so forming a non-binary rational number that could be used in a condition for checking that a required geometrical relationship is valid. Such a condition, for example that applies the values of the maximum deviations as weights for the parameters associated with the patches, will be apparent to those having ordinary skill in the art, and all such conditions and associated non-binary signal parameters are assumed to be comprised within the scope of the present invention.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method, comprising:
    receiving respective electrocardiograph (ECG) signals from body-surface electrodes at respective locations in proximity to a heart of a subject;
    processing the ECG signals to generate respective signal parameters thereof characteristic of positions of the body-surface electrodes with respect to the heart by finding baselines for the signals;
    generating the respective signal parameters by determining whether differences between maximum deviations from the baselines are positive or negative;
    enumerating as a first number the body-surface electrodes having a positive difference, and enumerating as a second number the body-surface electrodes having a negative difference, wherein achieving the specified geometrical relationship comprises the first and the second numbers differing by no more than a preset number; and
    adjusting the respective locations so as to achieve a specified geometrical relationship between the body-surface electrodes and the heart in response to the respective signal parameters.

2. The method according to claim 1, wherein the body-surface electrodes are configured to receive currents, from a catheter electrode within the subject, indicative of a location of the catheter electrode.

3. The method according to claim 2, wherein receiving the respective ECG signals comprises receiving the ECG signals while not receiving the currents.

4. The method according to claim 2, wherein receiving the respective ECG signals comprises receiving the ECG signals while receiving the currents.

5. The method according to claim 1, wherein the geometric relationship comprises the body-surface electrodes surrounding the heart.

6. The method according to claim 1 wherein the preset number comprises a positive whole number less than a total number of the body-surface electrodes.

7. The method according to claim 1, and comprising dividing the body-surface electrodes into a plurality of sub-groups, and comprising for a given sub-group enumerating as a first number the body-surface electrodes therein having a positive difference, and enumerating as a second number the body-surface electrodes therein having a negative difference, and wherein achieving the specified geometrical relationship comprises the first and the second numbers differing by no more than a preset number for the given sub-group.

8. The method according to claim 7, wherein the preset number comprises a positive whole number less than a total number of the body-surface electrodes in the given sub-group.

9. The method according to claim 1, wherein the signal parameters comprise binary parameters.

10. The method according to claim 1, wherein the signal parameters comprise non-binary parameters.

11. Apparatus, comprising:
    A plurality of body-surface electrodes, each body surface electrode positioned in a respective location in proximity to a heart of a subject, each body surface electrode configured to receive respective electrocardiograph (ECG) signals from the respective locations; and
    a controller, configured to process the ECG signals to generate respective signal parameters by finding baselines for the ECG signals and generating the signal parameters by determining whether differences between maximum deviations from the baselines are positive or negative and enumerating as a first number the body-surface electrodes having a positive difference, and enumerating as a second number the body-surface electrodes having a negative difference, and wherein achieving the specified geometrical relationship comprises the first and the second numbers differing by no more a preset number, and wherein the respective signal parameters are characteristic of the respective locations of the body-surface electrodes with respect to the heart, the controller further configured to adjust the respective locations so as to achieve a specified geometrical relationship between the body-surface electrodes and the heart in response to the respective signal parameters.

12. The apparatus according to claim 11, wherein the body-surface electrodes are configured to receive currents, from a catheter electrode within the subject, indicative of a location of the catheter electrode.

13. The apparatus according to claim 12, wherein receiving the respective ECG signals comprises receiving the ECG signals while not receiving the currents.

14. The apparatus according to claim 12, wherein receiving the respective ECG signals comprises receiving the ECG signals while receiving the currents.

15. The apparatus according to claim 11, wherein the geometric relationship comprises the body-surface electrodes surrounding the heart.

16. The apparatus according to claim 11, wherein the preset number comprises a positive whole number less than a total number of the body-surface electrodes.

17. The apparatus according to claim 11, and comprising the controller dividing the body-surface electrodes into a plurality of sub-groups, and for a given sub-group enumerating as a first number the body-surface electrodes therein having a positive difference, and enumerating as a second number the body-surface electrodes therein having a negative difference, and wherein achieving the specified geometrical relationship comprises the first and the second numbers differing by no more than a preset number for the given sub-group.

18. The apparatus according to claim 17, wherein the preset number comprises a positive whole number less than a total number of the body-surface electrodes in the given sub-group.

19. The apparatus according to claim 11, wherein the signal parameters comprise binary parameters.

20. The apparatus according to claim 11, wherein the signal parameters comprise non-binary parameters.

21. A method, comprising:
receiving respective electrocardiograph (ECG) signals from body-surface electrodes at respective locations in proximity to a heart of a subject;

processing the ECG signals to generate respective signal parameters thereof characteristic of positions of the body-surface electrodes with respect to the heart by finding baselines for the signals;

generating the respective signal parameters by determining whether differences between maximum deviations from the baselines are positive or negative;

dividing the body-surface electrodes into a plurality of sub-groups, and comprising for a given sub-group enumerating as a first number the body-surface electrodes therein having a positive difference, and enumerating as a second number the body-surface electrodes therein having a negative difference, and wherein achieving the specified geometrical relationship comprises the first and the second numbers differing by no more than a preset number for the given sub-group; and adjusting the respective locations so as to achieve a specified geometrical relationship between the body-surface electrodes and the heart in response to the respective signal parameters.

22. The method according to claim 21, wherein the body-surface electrodes are configured to receive currents, from a catheter electrode within the subject, indicative of a location of the catheter electrode.

23. The method according to claim 22, wherein receiving the respective ECG signals comprises receiving the ECG signals while not receiving the currents.

24. The method according to claim 22, wherein receiving the respective ECG signals comprises receiving the ECG signals while receiving the currents.

25. The method according to claim 21, wherein the geometric relationship comprises the body-surface electrodes surrounding the heart.

26. The method according to claim 21, wherein the preset number comprises a positive whole number less than a total number of the body-surface electrodes in the given sub-group.

27. The method according to claim 21, wherein the signal parameters comprise binary parameters.

28. The method according to claim 21, wherein the signal parameters comprise non-binary parameters.

* * * * *